(12) United States Patent
Matsubara et al.

(10) Patent No.: US 7,049,437 B2
(45) Date of Patent: May 23, 2006

(54) SYNTHETIC PROCESS AND CRYSTAL FORM OF CONDENSED IMIDAZOPYRIDINE DERIVATIVES

(75) Inventors: Fumihiko Matsubara, Osaka (JP); Takashi Ohya, Osaka (JP); Masaaki Uenaka, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 166 days.

(21) Appl. No.: 10/239,785

(22) PCT Filed: Mar. 29, 2001

(86) PCT No.: PCT/JP01/02620

§ 371 (c)(1),
(2), (4) Date: Sep. 25, 2002

(87) PCT Pub. No.: WO01/74821

PCT Pub. Date: Oct. 11, 2001

(65) Prior Publication Data

US 2003/0088102 A1 May 8, 2003

(30) Foreign Application Priority Data

Mar. 30, 2000 (JP) ............................. 2000-092565

(51) Int. Cl.
*C07D 513/00* (2006.01)
*C07D 513/02* (2006.01)
*C07D 491/00* (2006.01)

(52) U.S. Cl. .................... 544/48; 544/101; 544/250; 544/345; 546/82; 546/118

(58) Field of Classification Search ................ 546/118, 546/82; 544/101, 48, 250, 345
See application file for complete search history.

(56) References Cited

U.S. PATENT DOCUMENTS 5,378,848 A    1/1995  Takada et al. ................ 546/82
5,658,903 A *  8/1997  Adams et al. ............ 514/235.8

FOREIGN PATENT DOCUMENTS

EP            556008        8/1993

OTHER PUBLICATIONS

M. Adachi et al., "Intermolecular Transfer of . . . Pyridines", Tetrahedron Letters, vol. 37, No. 49, pp. 8871-8874, 1996.
M. Ichikawa et al., "Acidic Properties . . . Imidazole", Chem. Pharm. Bull., vol. 27, No. 5, pp. 1255-1264, 1979.
M. Adachi et al., "Intermolecular Transfer of an Alkenyl Group in Enamines: Application to Synthesis of [b]-Fused Pyridines", Tetrahedron Letters, vol. 37, No. 49, pp. 8871-8874, 1996.
M. Ichikawa et al., "Acidic Properties of Benzimidazoles and Substituent Effects. IV." Relationship Between the Acidities of N'-(Subtituted Phenyl)arylamidines and Ring Closures to Imidazole, Chem. Pharm. Bull, vol. 27, No. 5, pp. 1255-1264, 1979.
Abstract of the 23rd Congress of Heterocyclic Chemistry, pp. 97-99, 1992 with English translation.

* cited by examiner

*Primary Examiner*—Rita Desai
*Assistant Examiner*—Raymond Covington
(74) *Attorney, Agent, or Firm*—Wenderoth, Lind & Ponack, L.L.P.

(57) ABSTRACT

The present invention provides a process of a compound of the formula (I):

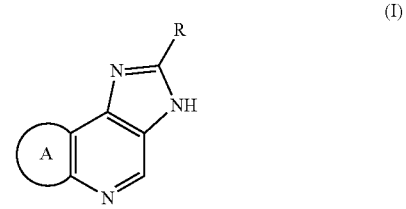

(I)

wherein R is heteroaryl or the like, ring A is a heteroalicyclic group or the like comprising reacting a compound of the formula (II):

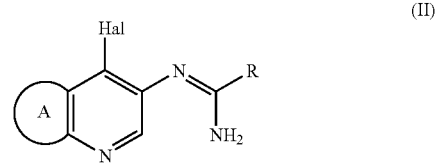

(II)

wherein Hal is halogen and the other symbols are the same as the above, in the presence of a sulfinic acid salt and further in the presence of an acid or a salt with an organic base, and a novel crystal form of 2-(3-isoxazolyl)-3,6,7,9-tetrahydroimidazo[4,5-d]pyrano[4,3-b]pyridine phosphate monohydrate.

5 Claims, 4 Drawing Sheets

SYNTHETIC PROCESS AND CRYSTAL FORM OF CONDENSED IMIDAZOPYRIDINE DERIVATIVES

This application is a U.S. national stage of PCT/JP01/02620 filed Mar. 29, 2001.

TECHNICAL FIELD

The present invention relates to a novel synthetic process and a novel crystal form of condensed imidazopyridine derivatives which are useful for pharmaceuticals.

BACKGROUND ART

Condensed imidazopyridine derivatives of the present invention are compounds described in JP 1993/286973A and known to be useful as psychotropic agents, antianxiety agents, anesthesia antagonistic agents, and cerebral function activators. In the above publication, a method for producing the condensed imidazopyridine derivatives which are cyclized by using N-methyl-2-pyrrolidone, biphenyl ether-biphenyl mixture etc. is described. But it was very difficult to use this method for industrial production because it is necessary to react at 150° C. to 250° C.

This publication only describes that 2-(3-isoxazolyl)-3,6,7,9-tetrahydroimidazo[4,5-d]pyrano[4,3-b]pyridine or salts thereof were obtained just as white crystals and does not indicate preferable crystal forms of phosphate or phosphate monohydrate.

Abstract of the 23rd Congress of Heterocyclic Chemistry, pp.97–99, 1992 discloses a reaction for obtaining heterocyclic sulfonyl compounds from its chloro compounds by using a sulfinic acid salt as a catalyst and thus obtained sulfonyl compounds are easily reacted by nucleophilic substitution of carbanions. But the publication does not suggest an affection by addition of a catalyst such as an acid or a salt of an organic base, specifically methanesulfonic acid.

DISCLOSURE OF INVENTION

The object of the present invention is to provide a novel synthetic process of condensed imidazopyridine derivatives, specifically 2-(3-isoxazolyl)-3,6,7,9-tetrahydroimidazo[4,5-d]pyrano[4,3-b]pyridine or salts thereof and a novel crystal form of phosphate salt thereof.

The present invention provides

[1] A process for producing a compound of the formula (I):

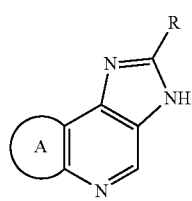

wherein R is optionally substituted aryl or optionally substituted heteroaryl and ring A is a 5- to 9-membered alicyclic group which may contain one or more of O, S, SO, $SO_2$ and/or $NR^1$ (wherein $R^1$ is hydrogen, alkyl, esterified carboxy, carbamoyl or acyl) and which may be substituted with alkyl (hereinafter referred to as Compound (I)), a pharmaceutical acceptable salt or solvate thereof comprising reacting a compound of the formula (II):

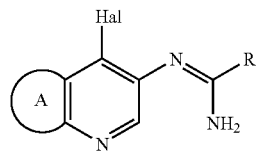

wherein Hal is halogen and the other symbols are the same as the above (hereinafter referred to as Compound (II)) in the presence of a sulfinic acid salt,

[2] The process as described in [1], wherein the reaction is carried out in the presence of a) an acid or b) a salt with an organic base,

[3] The process as described in [1] or [2] wherein R is 3-isoxazolyl and ring A is

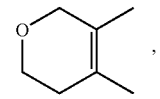

[4] The process as described in any one of [1] to [3] wherein the sulfinic acid salt is a para-toluenesulfinic acid salt,

[5] The process as described in any one of [2] to [4] wherein the acid is methanesulfonic acid,

[6] The process as described in any one of [2] to [5] wherein the reaction temperature is 120° C. or lower,

[7] A crystal of 2-(3-isoxazolyl)-3,6,7,9-tetrahydroimidazo[4,5-d]pyrano[4,3-b]pyridine phosphate monohydrate of the formula (Ia):

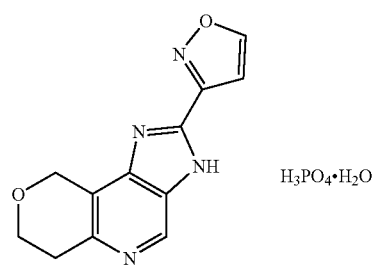

(hereinafter referred to as Compound (Ia)), which has a powder X-ray diffraction pattern having main peaks at diffraction angle (2θ)=15.3, 17.8, 26.2, 11.6, 20.9, 25.7 and 27.9 (degree) and

[8] The crystal as described in [7] which has a melting point of 162 to 175° C.

BEST MODE FOR CARRYING OUT THE INVENTION

Figure 1:
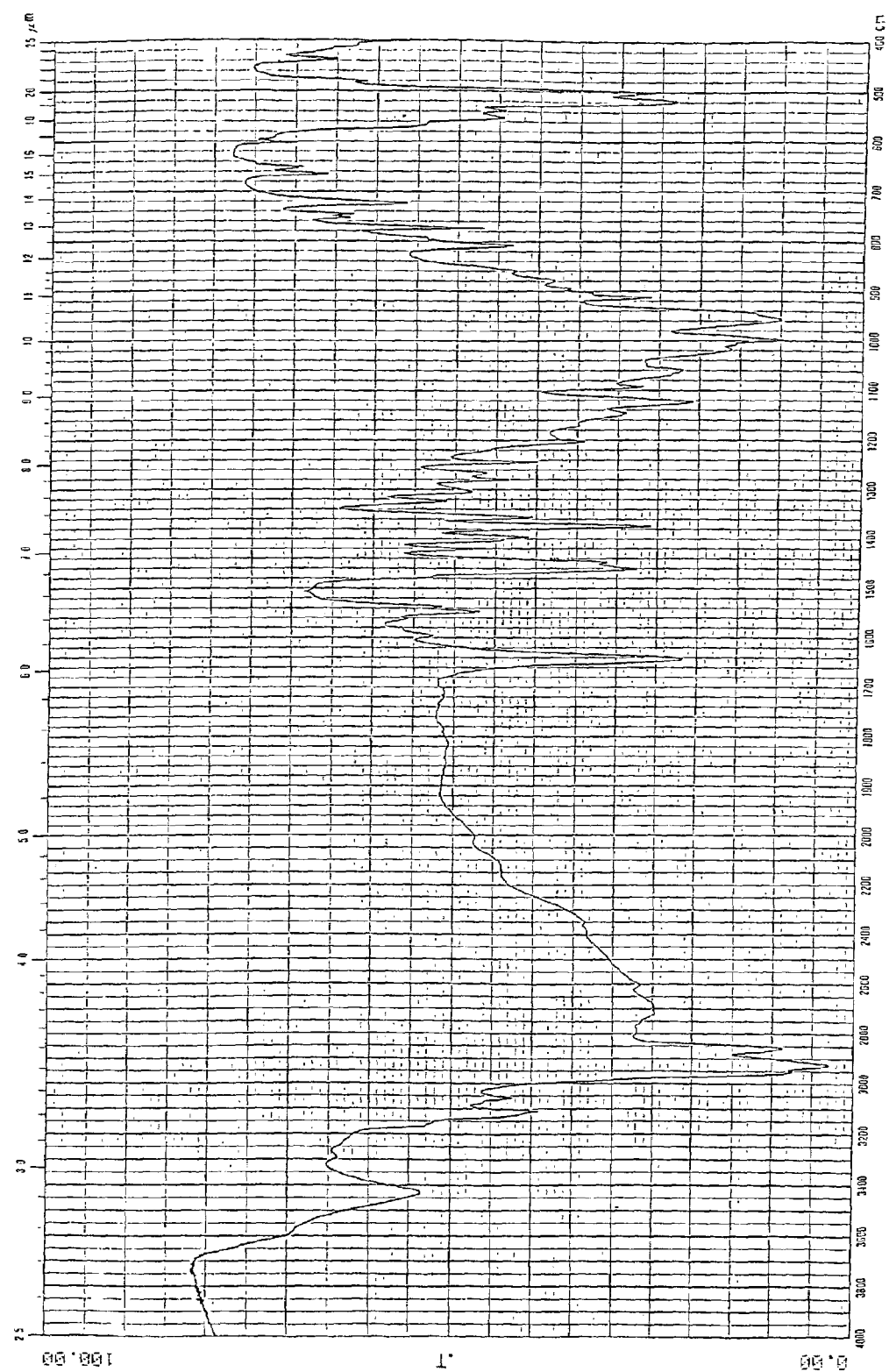
FIG. 1 shows powder X-ray diffraction chart of prism crystals.
Figure 2:
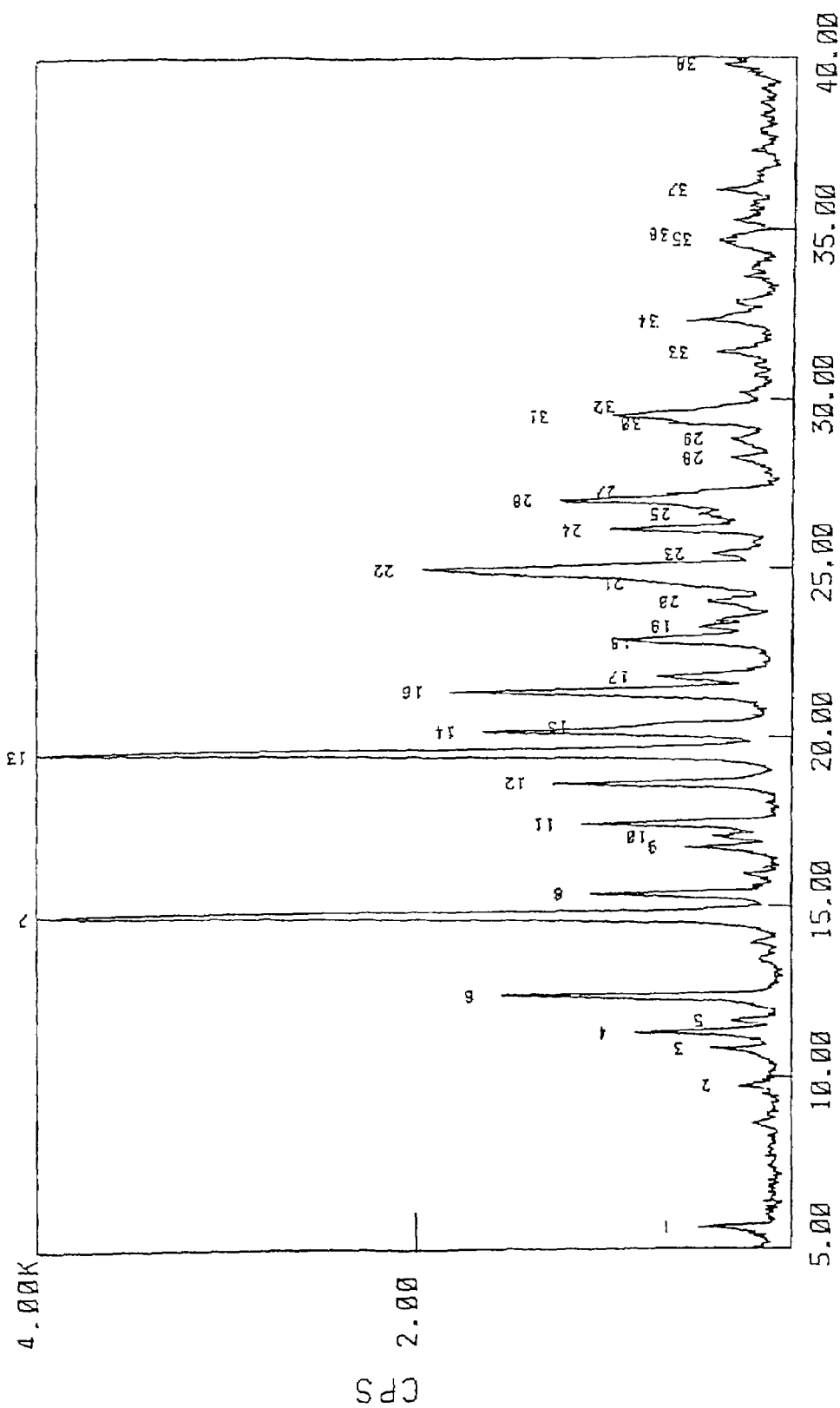
FIG. 2 shows infrared absorption spectrum chart of prism crystals.
Figure 3:
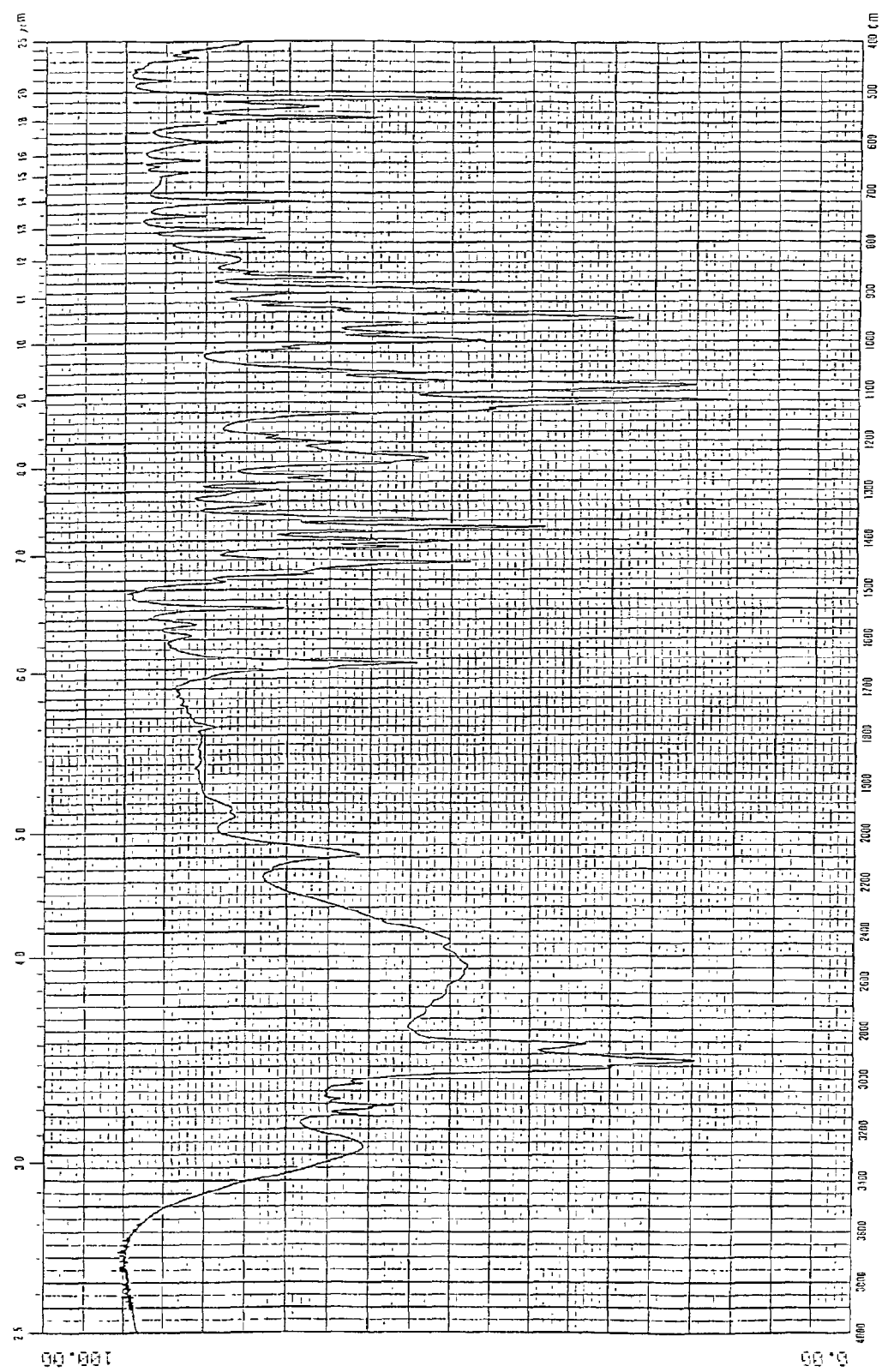
FIG. 3 shows powder X-ray diffraction chart of needle crystals.
Figure 4:
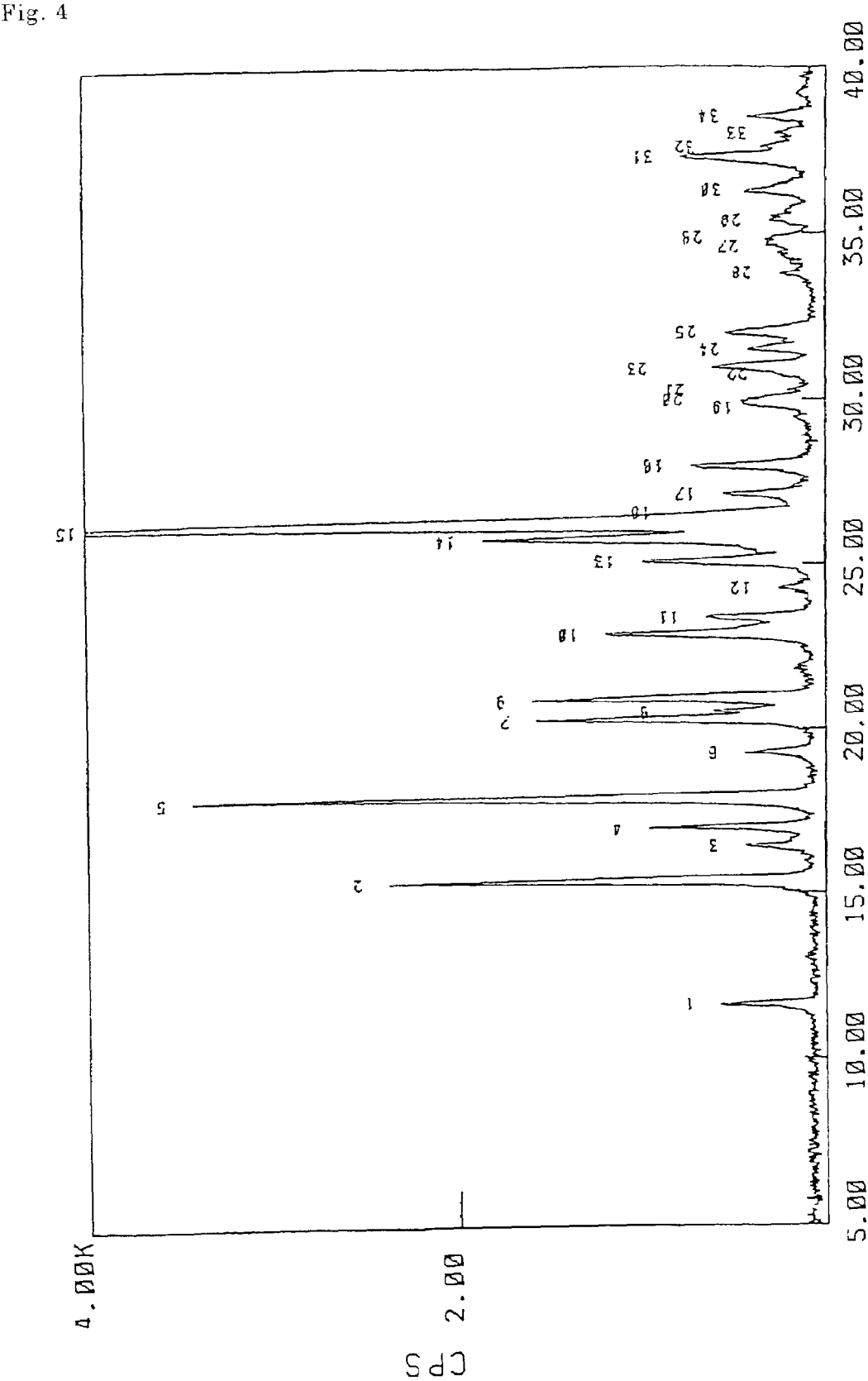
FIG. 4 shows infrared absorption spectrum chart of needle crystals.

In the present description, "halogen" includes fluorine, chlorine, bromine and iodine. Chlorine is preferable.

In the present specification, the term "aryl" includes phenyl, naphthyl, anthryl, indenyl, phenanthryl and the like.

The term "optionally substituted aryl" includes the above mentioned "aryl" which may have one or more of substituents selected from alkyl, hydroxy, alkoxy, aryloxy, acyloxy, carboxy, ester (e.g., alkoxycarbonyl, aralkoxycarbonyl etc.), cyano, amino, mono- or di-substituted amino, hydrazino, hydroxyamino, halogen, nitro, acyl, carbamoyl, thiocarbamoyl, carbamoyloxy, thiocarbamoyloxy, ureido, thioureido, sulfonamide, mono- or di-substituted sulfonamide, sulfonic acid, halogenoalkyl, hydroxyalkyl, alkoxyalkyl, acyloxyalkyl, nitroalkyl, aminoalkyl, acylaminoalkyl, cyanoalkyl, carboxyalkyl and the like. Preferable examples are substituted or unsubstituted phenyl and the examples of substituents for phenyl are methyl, methoxy, chloro and the like.

The term "heteroaryl" means a cyclic group containing one or more of hetero atoms optionally selected from O, S and N in the ring and the cyclic group may condense with a carbocycle or another heterocycle. The examples of "heteroaryl" are 5- to 6-membered heteroaryl such as pyrrolyl, imidazolyl, pyrazolyl, pyridyl, pyridazinyl, pyrimidinyl, pyrazinyl, triazinyl, isoxazolyl, oxazolyl, oxadiazolyl, isothiazolyl, thiazolyl, thiadiazolyl, furyl, thienyl etc., and condensed heteroaryl such as indolyl, benzimidazolyl, indazolyl, indolizinyl, quinolyl, isoquinolyl, cinnolinyl, phthalazinyl, quinazolinyl, naphthyridinyl, quinoxalinyl, pteridinyl, benzisoxazolyl, benzoxazolyl, oxadiazolyl, benzoxadiazolyl, benzisothiazolyl, benzothiazolyl, benzothiadiazolyl, benzofuryl, benzothienyl, carbazolyl, phenazinyl etc.

As the substituents for "optionally substituted heteroaryl", exemplified are alkyl, hydroxy, alkoxy, carboxy, ester (e.g., alkoxycarbonyl, aralkoxycarbonyl etc.), cyano, amino, mono- or di-substituted amino, hydrazino, hydroxyamino, halogen, nitro, acyl, carbamoyl, thiocarbamoyl, carbamoyloxy, thiocarbamoyloxy, ureido, thioureido, sulfonamide, mono- or di-substituted sulfonamide, sulfonic acid, halogenoalkyl, hydroxyalkyl, alkoxyalkyl, acyloxyalkyl, nitroalkyl, aminoalkyl, acylaminoalkyl, cyanoalkyl, carboxyalkyl and the like. These substituents may substitute at one or more of possible positions. The substituents are preferably unsubstituted 5-membered heteroaryl, more preferably unsubstituted thienyl, unsubstituted furyl, unsubstituted isoxazolyl or unsubstituted pyridyl, and most preferably unsubstituted isoxazolyl.

"A 5- to 9-membered alicyclic group which may contain one or more of O, S, SO, $SO_2$ and/or $NR^1$ wherein $R^1$ is hydrogen, alkyl, esterified carboxy, carbamoyl or acyl, and which may be substituted with alkyl" condenses with the neighboring pyridine ring. The examples of alicyclic groups are a carbocyclic group such as a cyclopenteno ring, a cyclohexeno ring, a cyclohepteno ring, a cycloocteno ring, a cyclononeno ring etc., a heteroalicycle such as pyrrolidino, pyrrolino, imidazolidino, pyrazolidino, dihydrothiopheno, dihydrofurano, thiazolino, dihydropyranno, dihydrothiopyrano, piperidino, piperazino, morpholino, thiomorpholino, tetrahydropyridino, and tetrahydropyrimidino etc. Dihyclropyrano, dihydrothiopyrano or piperidino is preferable and dihydropyrano is especially preferable. These rings may be substituted with alkyl (e.g., one or two methyl, ethyl or the like).

The term "alkyl" includes a straight or branched alkyl having 1 to 10 carbon atoms and a lower alkyl having 1 to 6 carbon atoms is preferable. For example, methyl, ethyl, n-propyl, isopropyl, n-butyl, isobutyl, sec-butyl, tert-butyl, n-pentyl, isopentyl, neopentyl, tert-pentyl, 2-metbylbutyl, n-hexyl, isohexyl, heptyl, isoheptyl, octyl, isooctyl, nonyl, decyl and the like are included.

The alkyl parts of "halogenoalkyl", "hydroxyalkyl", "alkoxyalkyl", "acyloxyalkyl", "nitroalkyl", "aminoalkyl", "acylaminoalkyl", "cyanoalkyl" and "carboxyalkyl" are the same as the above "alkyl".

The term "esterified carboxy" includes alkoxycarbonyl, aryloxycarbonyl and aralkoxycarbonyl and the like. The examples are methoxycarbonyl, ethoxycarbonyl, tert-butoxycarbonyl, benzyloxycarbonyl and the like.

The term "acyl" includes an aliphatic acyl having 1 to 10 carbon atoms and an aromatic acyl. The examples are formyl, acetyl, propionyl, butyryl, isobutyryl, valeryl, pivaloyl, hexanoyl, acryloyl, propioloyl, methacryloyl, crotonoyl, cyclohexanecarbonyl, benzoyl, 4-nitrobenzoyl, 4-tert-butylbenzoyl, benzenesulfonyl, toluenesulfonyl and the like.

The term "alkoxy" includes straight or branched alkoxy having 1 to 10 carbon atoms and a lower alkoxy having 1 to 6 carbon atoms is preferable. The examples are methoxy, ethoxy, n-propoxy, isopropoxy, n-butoxy, isobutoxy, sec-butoxy, tert-butoxy, n-pentyloxy, isopentyloxy, neopentyloxy, tert-pentyloxy, 2-methylbutoxy, n-hexyloxy, isohexyloxy, heptyloxy, isoheptyloxy, octyloxy, isooctyloxy, nonyloxy, decyloxy and the like.

The alkoxy parts of "alkoxycarbonyl", "alkoxyalkyl" and "aralkoxycarbonyl" are the same as the above "alkoxy".

The aryl parts of "aryloxy", "aryloxycarbonyl" and "aralkoxycarbonyl" are the same as the above "aryl".

The acyl parts of "acyloxy", "acylaminoalkyl" and "acyloxyalkyl" are the same as the above "acyl".

The substituents for "mono- or di-substituted amino" and "mono- or di-substituted sulfonamide" include one or two of hydroxy, halogen, alkyl, alkenyl, acyl, aryl and the like.

"Compound (I)" includes any possible pharmaceutically acceptable salt of each compound. As the "pharmaceutically acceptable salt", exemplified are salts with mineral acids such as hydrochloric acid, sulfuric acid, nitric acid, phosphoric acid, hydrofluoric acid, hydrobromic acid and the like; salts with organic acids such as formic acid, acetic acid, tartaric acid, lactic acid, citric acid, fumaric acid, maleic acid, succinic acid, methanesulfonic acid, benzenesulfonic acid, p-toluenesulfonic acid and the like; salts with acidic amino acids such as ornithine, aspartic acid, glutamic acid and the like. Phosphate is preferable.

Compound (I) includes solvate thereof, wherein arbitrary numbers of suitable organic solvent or water molecules may coordinate to Compound (I). Hydrate is preferable and monohydrate is more preferable.

Compound (I) includes three kinds of tautomers and the above mentioned formula ) is just an example. Compound (I) includes other tautomers, i.e., Compound (I') having double bonds at the 2–3, 3a–3b and 4–5 position and Compound (I") having double bonds at the 1–3b, 2–3 and 3a–4 position of the following formulae.

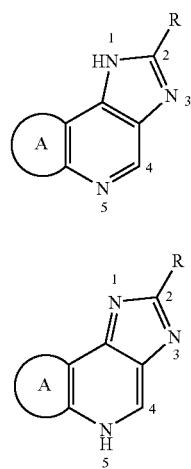

Compound (I) can be obtained from Compound (II) by the following reactions.

Compound (II) is reacted in a suitable solvent such as dimethylformamide, dimethylsulfoxide, N, N-dimethylimidazolidinone, N-methylpyrrolidone, dimethylacetoamide and Dautherm A in the presence of a sulfinic acid salt for several tens minutes to several hours. The examples of a sulfinic acid salt are sodium para-toluenesulfinate, potassium para-toluenesulfinate, lithium para-toluenesulfinate, sodium methanesulfinate, potassium methanesulfinate and lithium methanesulfinate. The upper limit of the reaction temperature is around 150° C., preferably around 145° C. and lower limit is around 90° C., preferably around 100° C.

The above reaction is preferably subjected to further in the presence of "an acid" or "a salt with an organic base" in addition to the presence of a sulfinic acid salt. The examples of "an acid" are methanesulfonic acid and para-toluenesulfinic acid. "A salt with an organic base" is preferably a salt which has pKb 5 or lower, for example, hydrochloride or hydrobromide with pyridine, N-methylmorpholine, N,N-dimethylpyridine or the like, hydrochloride, hydrobromide or methanesulfonate of Compound (I).

When the desired compounds are synthesized in the presence of "a) an acid or b) a salt with an organic base" and a sulfinic acid salt, the reaction may be conducted at about 130° C. or lower, preferably about 120° C. or lower, and most preferably about 100° C. or lower. The lower limit for suitably conducting this reaction is about 90° C., preferably about 100° C.

The present reaction which is conducted in the presence of an acid or a salt with an organic base is very useful for inexpensive and simple industrial production of Compound (I) because of escaping the high temperature reaction described in JP 1993/286973 A.

Compound (I) obtained by the present method can be turned into a free compound, hydrochloride, methanesulfonate, maleate, phosphate or the like by the conventional method. For example, methanesulfonate can be turned into a free compound by treating with sodium hydroxide. A free compound can be crystallized as phosphate by treating with an aqueous solution containing phosphoric acid (for example, 20% aqueous isopropanol).

Two kinds of crystal forms, i.e., prism crystals and needle crystals were found as crystals of Compound (Ia), one of Compound (I) which can be obtained by the above method. These crystals are distinguished by characteristic peaks of powder X-ray diffraction or absorption bands of infrared absorption spectrum.

For example, prism crystals can be obtained by the following method.

Firstly, a free compound, a salt or solvate of 2-(3-isoxazolyl)-3,6,7,9-tetrahydroimidazo[4,5-d]pyrano[4,3-b]pyridine is obtained by the method described in JP 1993/2286973A or the above-mentioned method. Thus obtained compound (for example, phosphate) is suspended in a diluted aqueous solution of phosphoric acid (about 0.01 equivalent, preferably 0.05 equivalent). The suspension is stirred or allowed to stand under cooling or at room temperature for several hours to recrystallize, and needle crystals of Compound (Ia) are obtained.

Free compound or hydrate of 2-(3-isoxazolyl)-3,6,7,9-tetrahydroimidazo[4,5-d]pyrano[4,3-b]pyridine may be crystallized as phosphate from an aqueous solvent (for example, aqueous methanol, aqueous ethanol, aqueous propanol, aqueous isopropanol and the like, preferably 20% aqueous isopropanol) containing phosphoric acid at the mole ratio of 1 to 2, preferably 1.2. Then, the obtained crystals may be recrystallized from a diluted aqueous solution of phosphoric acid in the similar manner as the above.

Thus obtained needle crystals are suspended in a diluted aqueous solution of phosphoric acid again and are kept with stirring or on standing for about 1 to 3 days to obtain prism crystals. Prism crystals of Compound (Ia) can be obtained when needle crystals are stirred with heating at about 30 to 100° C., preferably 60 to 100° C. for several tens minutes to several hours. When recrystallization is carried out by adding seed crystals already prepared, the desired crystals are obtained effectively.

Prism crystals of Compound (Ia) are preferable because of high stability to heat and light as compared with needle crystals. Prism crystals have another advantage of good operation in synthetic processes because they are easily separated from a solvent by filtration. Furthermore, prism crystals are stable and high quality at ordinary temperature and atmospheric pressure because water molecules are contained in prism crystal structure as crystal water by making hydrogen binding.

Melting point of prism crystals of Compound (Ia) is 162 to 175° C., more closely 167 to 170° C. The determination can be conducted according to the melting point determination method in pharmacopoeia of Japan.

The present invention is further explained by the following Examples and Experiments, which are not intended to limit the scope of the present invention.

EXAMPLES

In the following Examples, X-ray diffraction of Compound (Ia) was detected under the following conditions.
X-ray diffraction conditions:
Rigaku Corporation RAD-C, powder X-ray diffraction meter
Target: Cu, Graphite Monochrometer, Tube voltage: 40 kV, Tube current: 40 mA, Slit:
DS=0.5, RS=0/3, SS=0.1, Scan Speed: 3°/min, Detector Scintilation counter,
Sample cell: small diameter, for small amount of samples (φ 5 mm)

Example 1

Synthesis of 2-(3-isoxazolyl)-3,6,7,9-tetrahydroimidazo[4,5-d]pyrano[4,3-b]pyridine 1.25 g of Compound (II: Hal is Cl, R=3-isoxazolyl, ring A=dihydropyrano) was dissolved in 12 ml of DMF and 3.20 g of sodium para-toluenesulfinate was added. The solution was heated to 110° C. and 0.86 g of methanesulfonic acid was added. Solution of 3.75 g of Compound (II) in 12.5 ml of DMF was added dropwise over 1 hour at the same temperature. After the mixture was stirred for 1.5 hours at the same temperature and cooled, 40 ml of acetone was added to obtain a crude mixture salt (methanesulfonic acid salt and hydrochloride) of the titled compound.

Without drying, the obtained mixture salt was dissolved in 55.5 ml of water. 0.367 g of 96% sulfuric acid and 0.25 g of activated carbon were added and the mixture was stirred at 60° C. After cooling, activated carbon was filtered off and 18.5 g of 4.8% sodium hydroxide was added to neutralize. Crystallized crystals were filtered to obtain 3.99 g of free compound dihydrate of the title compound (80% yield).

Example 2

Using a similar method of Example 1 except that the kind of sulfinic acid salt and existence or absence of acid, the desired compounds were synthesized and the affection of a sulfinic acid salt and acid was examined. Synthesized compound was 2-(3-isoxazolyl)-3,6,7,9-tetrahydroimidazo[4,5-d]pyrano[4,3-b]pyridine hydrochloride, which is described in JP 1993/286973 A. Number of mole equivalent in tables means the volume per 1 mole equivalent of Compound (II) and "1V" means 1 ml per 1 g of Compound (II).

necked flask equipped with a stirrer, a thermometer and a nitrogen gas tube, 1.97 L of N-methyl-2-pyrrolidone was poured therein to obtain a suspension. The suspension was reacted with stirring under mild nitrogen atmosphere for 50 minutes at 190 to 210° C. (internal temperature) in oil bath of 200° C. After the reacted mixture was cooled to 40° C., 2 L of acetone was added to obtain the suspension. The obtained suspension was poured into a 20 L 4 necked flask, 7.84 L of acetone was added and the mixture was cooled to 3° C. The precipitated crystals were filtered, washed twice with 1.3 L of acetone and air-dried for 18 hours to obtain 879 g of crude crystals of 2-(3-isoxazolyl)-3,6,7,9-tetrahydroimisazo[4,5-d]pyrano[4,3-b]pyridine (hydrochloride) (89.3%).

879 g of crude crystals were dissolved in 35.16 L of 20% aqueous isopropanol with heating and 505 ml of concentrated aqueous ammonia and 295 g of activated carbon were added. After the solution was refluxed for 20 minutes and activated carbon was filtered off, the filtrate was washed with 6.7 L of warmed 20% aqueous isopropanol and 3.3 L of isopropanol. The filtrate and wash liquid were mixed and concentrated under reduced pressure to obtain 9.95 kg of a concentrated solution. The obtained solution was cooled at 4° C. for 18 hours, precipitated crystals were filtered, washed twice with 1.8 L of ice-cooled 20% aqueous isopropanol and air-dried for 18 hours to obtain 764 g of the titled compound (77.8%).

mp>300° C.

Elementary Analysis ($C_{12}H_{10}N_4O_2 \cdot 2H_2O$)

Calcd.: C, 51.80; H, 5.07; N, 20.13; $H_2O$, 12.95%. Found: C, 51.85; H, 5.10; N, 20.30; $H_2O$, 12.71%.

TABLE 1

| sulfinic acid salt | | acid | | solvent | Reaction temperature (° C.) | Reaction time (hr) | Yield (%) |
|---|---|---|---|---|---|---|---|
| Lithium para-toluene-sulfinate | 1 mole equivalent | — | — | DMSO (2V) | 145 | 1 | 92.0 |
| Lithium para-toluene-sulfinate | 0.5 mole equivalent | — | — | DMSO (2V) | 145 | 2 | 93.0 |
| Sodium para-toluene-sulfinate | 0.5 mole equivalent | — | — | DMSO (2V) | 145 | 2 | 90.5 |
| Sodium para-toluene-sulfinate | 1 mole equivalent | Methane-sulfonic acid | 0.5 mole equivalent | NMP (4V) | 94–97 | 1 | 90.4 |
| Sodium para-toluene-sulfinate | 1 mole equivalent | Methane-sulfonic acid | 0.5 mole equivalent | NMP (4V) | 94–97 | 2 | 94.0 |

NMP: N-methyl-2-pyrrolidone
DMSO: dimethylsulfoxide

Reference Example 1

Synthesis of 2-(3-isoxazolyl)-3,6,7,9-tetrahydroimidazo[4,5-d]pyrano[4,3-b]pyridine (free compound, dihydrate)

After 984 g of Compound (II: Hal=Cl, R=3-isoxazolyl, ring A=dihydropyrano) (3.53 mol) was added in a 5 L 4

Reference Example 2

Preparation of Needle Crystals

To 764 g of the compound obtained in Reference Example 1 (free compound, dihydrate) in a 30 L reaction chamber, 26.75 L of 20% aqueous isopropanol was added and dissolved with stirring under heating at 80 to 84° C. 76.4 g of activated carbon was added and the mixture was stirred for 30 minutes at the same temperature. After the activated carbon was filtered off, the activated carbon was washed with 3.4 L of warmed 20% aqueous isopropanol. The filtrate and wash liquid were mixed and transported to a 60 L crystallizer. The solution was warmed to 78° C. to dissolve precipitated crystals, a solution of 389 g of 85% phosphoric acid (1.23 mol equivalent) in 389 ml of isopropanol was added and the dropping vessel was washed with 400 ml of isopropanol. Though needle crystals were precipitated after one minute and the whole mixture was solidified, it turned to be a suspension by stirring at high speed. Thus obtained suspension was cooled to 4° C. and allowed to stand for 18 hours. After the suspension was took out from the crystallizer, it was filtered, washed twice with 4.6 L of isopropanol and air-dried at room temperature for 18 hours to obtain 946.5 g of Compound (Ia) as needle crystals (96.2%).

mp 234–236° C.

Elementary Analysis ($C_{12}H_{10}N_4O_2 \cdot H_3PO_4 \cdot H_2O$)

Calcd.: C, 40.23; H, 4.22N, 15.63; P, 8.65; $H_2O$, 5.03%. Found: C, 40.39; H, 4.17N, 15.92; P, 8.53; $H_2O$, 4.10%.

powder X-ray diffraction: 12.4, 14.7, 17.4, 19.6, 21.4, 25.0, 27.0 (degree)

IR: 3426, 3109, 1642, 1123, 998, 957 and 808 ($cm^{-1}$)

Example 3

Preparation of Prism Crystals

To 3119 g of needle crystals (8.705 mol) obtained in Reference Example 2 in a 30 L enamel bat equipped with a stirrer, 18.71 L of distilled water containing 50.18 g of 85% phosphoric acid (0.05 mol equivalent) was added to obtain a suspension. Crystalline nucleus already prepared was added and stirred at room temperature (23 to 24° C.) for 43 hours. The precipitated crystals were filtered, washed twice with 1.5 L of ice-cooled distilled water and dried under reduced pressure at room temperature for 4 days to obtain 2902 g of Compound (Ia) as prism crystals (93.1%).

mp 167 to 170° C. (formed fusion)

dp 242 to 252° C. (colored fusion)

Elementary Analysis ($C_{12}H_{10}N_4O_2 \cdot H_3PO_4 \cdot H_2O$)

Calcd.: C, 40.23; H, 4.22N, 15.63; P, 8.65; $H_2O$, 5.03%. Found: C, 40.25; H, 4.26N, 15.71; P, 8.64; $H_2O$, 5.16%.

powder X-ray diffraction: 11.6, 15.3, 17.8, 20.9, 25.7, 26.2 and 27.9 (degree)

IR: 3264, 3104, 2533, 2085, 1648, 1119, 1089, 954 and 513 ($cm^{-1}$)

In the following Experiments, contents of Compound (I) were determined by HPLC under the following conditions.

Device: WATERS 510, 481, 712 WISP, 741, FD20A or WATERS 510, 486, 712 WISP, 741, FD20A Column: YMC-packed column AM-302 S-5 120A ODS (4.6 mm φ×150 mm)

Column temperature: room temperature

Mobile phase: methanol/water/TFA=200/800/1 (v/v)

Flow rate: 1.0 ml/min

Wave length: 230 nm

Concentration: 5–85 μg/ml

Injection Volume: 15 μl

Purity of Compound (I) was observed by HPLC peaks detected by WATERS 991 Photodiode Array Detector.

Experiment 1 Stability to Heat

Prism crystals and needle crystals of Compound (Ia) were used for samples. About 25 mg of each crystal was put in a small glass container with polyethylene cap. Containers were capped, sealed with PARAFILM and kept at 40° C., relative humidity of 75% for 6 months. Prism crystals were not observed appearance transition and needle crystals changed its color to pale yellow.

These results show prism crystals are more stable to heat compared with needle crystals.

Experiment 2 Stability to Light

After samples were prepared in the same manner of Experiment 1 and sealed, they were kept under 1800 Lux exposure (16 hours exposure per day of a fluorescent lamp, 28800 Lux*hr/day) or under 10000 Lux exposure (continuous exposure of a fluorescent lamp, 240000 Lux*hr/day, average temperature 30±3° C.). As a standard reference sample, each of crystals was put in a sealed container and kept at −20° C. The content of crystals were determined by the absolute calibration curve method using HPLC under the above conditions. Results of observation of appearance transition and remaining rate are shown below.

TABLE 2

| | | Prism crystals | | Needle crystals | |
| --- | --- | --- | --- | --- | --- |
| | | appearance | remaining rate (%) | appearance | remaining rate (%) |
| 1800Lux | 1 month | − | 100.0 | ± or + | 98.6 |
| | 2 months | − | 99.9 | + | 98.3 |
| | 3 months | − or ± | 100.1 | ++ | 96.9 |
| | 4 months | ± | 100.1 | ++ | 97.0 |
| 10000Lux | 1 week | ± | 99.5 | ± or + | 99.3 |
| | 2 weeks | ± or + | 99.7 | + | 98.0 |
| | 3 weeks | + | 99.2 | + or ++ | 97.4 |

As shown the above, needle crystals changed the color to yellow and their remaining rate decreased after 3 months. Prism crystals scarcely changed appearance and their remaining rate are more stable to light.

INDUSTRIAL APPLICABILITY

As shown in the above examples and experiments, the present process of Compound (I) is useful for mass-production. Prism crystals of Compound (Ia) is exhibiting high stability and very useful for pharmaceutical raw materials.

The invention claimed is:

1. A process for producing a compound of formula (I):

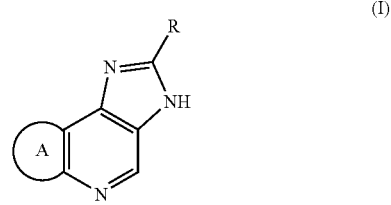

(I)

wherein R is optionally substituted aryl or optionally substituted heteroaryl and ring A is a 5- to 9-membered alicylic group which may contain one or more of O, S, SO, $SO_2$ and/or $NR^1$ wherein $R^1$ is hydrogen, alkyl, esterified carboxy, carbamoyl or acyl and which may be substituted with alkyl, or a pharmaceutically acceptable salt or solvate thereof, comprising reacting a compound of formula (II):

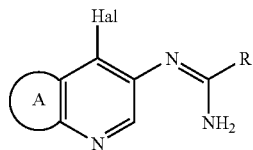
(II)

wherein Hal is halogen and the other symbols have the same meaning as defined above, in the presence of a sodium para-toluenesulfinate salt.

2. The process as claimed in claim 1, wherein the reaction is carried out in the presence of a) an acid or b) a salt of an organic base.

3. The process as claimed in claim 1 wherein R is 3-isoxazolyl and ring A is

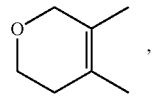
,

4. The process as claimed in claim 2 wherein the acid is methanesulfonic acid.

5. The process as claimed in claim 2 wherein the reaction temperature is 120° C. or lower.

* * * * *